(12) United States Patent
Valiev et al.

(10) Patent No.: US 8,919,168 B2
(45) Date of Patent: Dec. 30, 2014

(54) NANOSTRUCTURED COMMERCIALLY PURE TITANIUM FOR BIOMEDICINE AND A METHOD FOR PRODUCING A ROD THEREFROM

(76) Inventors: Ruslan Zufarovich Valiev, Ufa (RU); Irina Petrovna Semenova, Ufa (RU); Evgeniya Borisovna Yakushina, Ufa (RU); Gul'naz Khalifovna Salimgareeva, Ufa (RU)

( * ) Notice: Subject to any disclaimer, the term of this patent is extended or adjusted under 35 U.S.C. 154(b) by 611 days.

(21) Appl. No.: 13/122,063
(22) PCT Filed: Oct. 20, 2009
(86) PCT No.: PCT/RU2009/000556
§ 371 (c)(1), (2), (4) Date: Mar. 31, 2011
(87) PCT Pub. No.: WO2010/047620
PCT Pub. Date: Apr. 29, 2010

(65) Prior Publication Data
US 2011/0179848 A1 Jul. 28, 2011

(30) Foreign Application Priority Data
Oct. 22, 2008 (RU) .............................. 2008141956

(51) Int. Cl.
*B21C 23/00* (2006.01)
*A61L 27/06* (2006.01)
*C22C 14/00* (2006.01)
*C22F 1/18* (2006.01)

(52) U.S. Cl.
CPC ............... *A61L 27/06* (2013.01); *C22C 14/00* (2013.01); *C22F 1/183* (2013.01); *A61L 2400/12* (2013.01); *Y10S 72/70* (2013.01); *Y10S 623/925* (2013.01)
USPC ............. 72/253.1; 72/700; 428/544; 623/925

(58) Field of Classification Search
USPC ......... 72/253.1, 340, 364, 700; 148/668, 669, 148/670; 428/544, 545, 546, 660; 623/925; 977/810
See application file for complete search history.

(56) References Cited

U.S. PATENT DOCUMENTS 6,399,215 B1 * 6/2002 Zhu et al. ...................... 428/544
6,565,683 B1 * 5/2003 Utyashev et al. ............. 148/624

(Continued)

FOREIGN PATENT DOCUMENTS

DE 4006379 A1 4/1991
KR 2002-0074843 A 10/2002

(Continued)

OTHER PUBLICATIONS

"Microstructure development during equal-channel angular pressing of titanium", Shin et al. Oct. 2003.*

(Continued)

*Primary Examiner* — Edward Tolan
(74) *Attorney, Agent, or Firm* — Alexander Rabinovich

(57) ABSTRACT

Commercially pure titanium having UFG structure and enhanced mechanical and biomedical characteristics has nanocrystalline alpha-phase grains with a hexagonal close-packed lattice, in which the share of grains with a size of 0.1 ... 0.5 μm and a grain shape coefficient of no more than 2 in the mutually perpendicular planes makes no less than 90%, over 60% of the grains having high-angle boundaries disoriented in relation to the adjacent grains by the angles from 15 to 90°.

The method for making a rod of the material provides for equal-channel angular pressing of a billet at T≤450° C. with the total accumulated true strain e≥4 to effect severe plastic deformation of the billet and subsequent thermomechanical treatment with a gradual decrease of the temperature in the range of 450 ... 350° C. and the strain rate of $10^{-2} ... 10^{-4}$ s$^{-1}$ with the strain degree from 40 to 80% to effect additional plastic deformation.

10 Claims, 4 Drawing Sheets

(56) References Cited

U.S. PATENT DOCUMENTS

| | | | |
|---|---|---|---|
| 6,878,250 B1* | 4/2005 | Segal et al. | 204/298.13 |
| 6,946,039 B1* | 9/2005 | Segal et al. | 148/400 |
| 8,613,818 B2* | 12/2013 | Forbes Jones et al. | 148/649 |
| 2003/0223902 A1* | 12/2003 | Fukai et al. | 420/420 |
| 2006/0213592 A1* | 9/2006 | Ko et al. | 148/670 |
| 2008/0138163 A1* | 6/2008 | Moscoso et al. | 407/115 |
| 2009/0020192 A1* | 1/2009 | Segal et al. | 148/536 |
| 2012/0160378 A1* | 6/2012 | Park et al. | 148/670 |

FOREIGN PATENT DOCUMENTS

| | | |
|---|---|---|
| RU | 2146535 C1 | 3/2000 |
| RU | 2175685 C1 | 11/2001 |
| RU | 2251588 C2 | 5/2005 |
| RU | 2277992 C2 | 6/2006 |

OTHER PUBLICATIONS

International Search Report from PCT/RU2009/000556 dated Mar. 10, 2010 (2 pages).

G. KH. Sadikova et al.. Vliyanie intensivnoi plasticheskoi deformatsii i termomekhanicheskoi obrabotki na strukturu i svoistva titana, Metallovedenie i termicheskaya obrabotka metalov N° 11 (605), Nov. 2005, pp. 31-34.

Brunette et al. "Titanium in Medicine" ISBN 3-540-66936-1 Springer-Verlag Berline Heidelberg New York, pp. 15-18 and 91 (7 pages), Jan. 2001.

English Abstract of RU 2251588. (1 page), May 2005.
English Abstract of RU 2277992. (1 page), Jun. 2006.
English Abstract of DE 4006379. (1 page), Jun. 2004.
English Abstract of RU 2146535. (1 page), Nov. 2001.
English Abstract of RU 2175685. (1 page), Mar. 2000.
English Abstract of KR 2002-0074843. (1 page), Apr. 1991.

* cited by examiner

NANOSTRUCTURED COMMERCIALLY PURE TITANIUM FOR BIOMEDICINE AND A METHOD FOR PRODUCING A ROD THEREFROM

CROSS-REFERENCE TO RELATED APPLICATIONS

This application is a U.S. National phase application of the International application WO 2010/047620 A1 (PCT/RU2009/000556), filed Oct. 20, 2009, and claims priority to application 2008141956 filed on Oct. 22, 2008, in the Russian Federation, the both applications being hereby incorporated by reference in their entirety.

BACKGROUND OF THE INVENTION

1. Field of the Invention

The present invention relates to nanostructural materials with ultrafine-grained (UFG) structure and enhanced mechanical and biomedical characteristics and, more particularly, to titanium and its alloys that may be used for making medical implants applied in surgery, orthopedics, traumatology, and dentistry, as well as to a technology for processing these materials for forming structures that ensure specific mechanical and biomedical properties.

2. Description of Related Art

It has been known that strength, reliability, and durability of an implant depend on chemical composition, and mechanical and biomedical characteristics of the material it is made of. At the same time, microstructure plays a key role in establishment of strength, plasticity, fatigue, corrodibility, and biocompatibility in a specific material. Depending on the processing method, the microstructure is able to have various phase composition, size and shape of grains, disorientation of their boundaries, the density of dislocations and other crystalline lattice defects, etc. (M. A. Shtremel, Strength of Alloys, part 1: Lattice defects, 280 pp, Moscow, Metallurgy, 1982; M. A. Shtremel, Strength of Alloys, part 2: Deformation, Moscow, MISiS, 1997, 527 pp., pp 82-113).

Commercially pure titanium has been widely used in manufacturing implants for dentistry and traumatology due to its high biocompatibility (D. M. Brunette, P. Tengvall, M. Textor, P. Thomsen, "Titanium in medicine", Springer, 2001, 1019 pp., pp. 562-570, paragraphs 17.1, 17.2).

Also, Russian patent RU 2146535, A61C 8/00, A61L 27/00, of Mar. 20, 2000, describes a method for manufacturing intraosseous dental implant from titanium. As commercially pure titanium does not possess high strength characteristics, a multilayered bioactive coating is used in this case in order to increase the mechanical strength of the implant. The coating comprises five various layers applied in succession with the help of plasma spraying.

Enhanced mechanical strength of an implant can also be achieved by the use of high titanium-based alloys. For instance, patent KR20020074843, A61L 27/06, A61L 27/00, published on Oct. 4, 2002, discloses a method for making a removable bone prosthesis of titanium alloys Ti6Al4V, Ti5Al2.5Sn, Ti3Al13V11Cr, Ti15Mo5Zr3Tl, or Ti6Al12NbTa. However, the values of biocompatibility of high titanium alloys are considerably lower than those of commercially pure titanium. Prolonged staying of implants made of those alloys in a human body can result in accumulation of toxic elements such as vanadium and chromium [D. M. Brunette, et al. Ibid]. That is why, to enhance biocompatibility and optimize the process of osseointegration, bioinert coating of calcium hydroxyapatite (bone-salt) powder is applied onto the implant surface in a vacuum furnace upon heating up to 800 . . . 1000° C.

So in the above mentioned patents commercially pure titanium is used for making implants, which can stay in a human body for long. Its main disadvantage, however, is moderate mechanical strength. In this connection, in order to enhance the strength properties of an implant, usually special biocompatible coating applied on the product surface or high titanium alloys with enhanced hardness, strength, and fatigue endurance are used. Biocompatibility of the implants from titanium alloys is achieved through application of biocompatible coatings. On the whole, employment of expensive titanium alloys as well as processes of applying biocoatings onto the product surface results in the increase of the implant net cost.

It is known that the formation of ultrafine-grained (UFG) structures, which contain mostly high-angle boundaries, allows getting a unique combination of strength, ductility, and fatigue endurance in metals and alloys. [R. Z. Valiev, I. V. Alexandrov. Bulk nanostructural metallic materials.—M.: IKC "Academkniga", 2007.—398 pp.].

Also known in the art has been commercially pure titanium with the UFG structure produced by combined techniques of severe plastic deformation [G. Kh. Sadikova, V. V. Latysh, I. P. Semenova, R. Z. Valiev "Influence of severe plastic deformation and thermo mechanical treatment on the structure and properties of titanium" Metal science and heat treatment of metals, No 11 (605), 2005, pp. 31-34]. The microstructure in the cross section of the billet is characterized by equiaxed grains and subgrains of the alpha-phase with a hexagonal close-packed (HCP) lattice with the average size of about 200 nm and high dislocation density. The indicated technical solution is taken as the closest analogue.

However, the structure in the longitudinal section of the billet investigated along the length of the rod in several areas has alpha-phase grains elongated along the direction of deformation with the length-to-width ratio (grain shape coefficient) of 6:1. The inner area of the elongated grains is fragmented mostly by low-angle dislocation boundaries. Material with such a structure is characterized by anisotropy of properties in the longitudinal and cross sections of the billet that has an adverse effect on the service life of medical implants.

There has been known a technique for processing rods of commercially pure titanium (RU patent No 22175685, C22F 1/18, published on Jul. 27, 2000), in which formation of a high-strength state is achieved by the microstructure refinement via equal-channel angular pressing (ECAP) with a subsequent thermo mechanical treatment. The thermo mechanical treatment includes interchange of cold deformation with the degree of 30-90% and intermediate and final annealing in the range of temperatures from 250 to 500° C. for 0.2-2 hours. As a result, an ultrafine-grained structure with the grain size of about 0.1 μm is formed in the rod-shaped billet.

The disadvantages of this method are a high degree of anisotropy in the structure and properties of the rod material due to heterogeneity of grain morphology in the longitudinal and cross sections of the billet, and a substantial fraction of low-angle boundaries. Such material possesses enhanced strength, but limited ductility, which does not provide sufficient resistance to fatigue failure.

BRIEF SUMMARY OF THE INVENTION

The object of the invention is to develop commercially pure titanium that ensures enhanced properties in relation to mechanical strength, resistance to fatigue failure, biomedical properties by means of nanocrystalline structure and also to develop an efficient method for producing rods therefrom.

The object to be sought is attained by providing a commercially pure titanium for biomedicine, which has a structure of nanocrystalline alpha-phase grains with a hexagonal close-packed lattice, characterized by that the volume fraction of grains with a size of 0.1 ... 0.5 µm and with a grain shape coefficient of no more than 2 in the mutually perpendicular planes makes up no less than 90% in the structure, more than 60% of the grains having high-angle boundaries disoriented in relation to the adjacent grains by the angles from 15 to 90°.

The object to be sought is attained by providing a method for making a rod of commercially pure titanium with nanocrystalline structure for biomedicine, the method comprising the steps of severe plastic deformation of a billet by the equal channel angular pressing at a temperature no more than 450° C. with the total true accumulated strain e≥4, and the subsequent thermo mechanical treatment with the strain degree from 40 to 80%, wherein the step of thermo mechanical treatment includes plastic deformation performed with a gradual decrease of temperature in the range T=450 ... 350° C. and the strain rate of $10^{-2} ... 10^{-4}$ s$^{-1}$.

The invention allows achieving a higher level of mechanical and fatigue properties, which is conditioned by the peculiarities of the nanostructure formed in commercially pure titanium in compliance with the method according to the invention.

Firstly, the enhancement of strength in titanium is conditioned by a very small grain size (0.1 ... 0.5 µm) in the structure, that provides an increase in the flow stress during plastic deformation in accordance with the known Hall-Petch ratio [Large plastic deformations and metal failure. Rybin V. V., M.: Metallurgy, 1986, 224 pp.]. Considerable increase of strength is achieved also due to the fact that it is high-angle grain boundaries, the total share of which is no less than 60%, that provide the largest contribution to strengthening, as compared to low-angle and special boundaries [R. Z. Valiev, I. V. Alexandrov. Bulk nanostructured metallic materials.—M.: "Academkniga", 2007.—398 pp.]. Along with that, during plastic deformation (for example, during tension), grains within this size range with high-angle boundary disorientation are able to demonstrate grain boundary slip (GBS). The GBS, being an additional deformation mechanism, is favorable to imparting ductility to the material [R. Z. Valiev, I. V. Alexandrov, ibid.], the formation of grains with the shape coefficient of not over 2 (width-to-length ratio of the grain being 1:2) reducing the heterogeneity of the plastic flow of the metal, the level of microstresses, and, thus, preventing the early localization of deformation that leads to material failure from occurring. The structure changes in the material described above are implemented by the proposed treatment technique under the specified temperature-rate regimes.

It is known that the UFG structure of commercially pure titanium provides its enhanced biocompatibility [D. M. Brunette, P. Tengvall, M. Textor, P. Thomsen, "Titanium in medicine", Springer, (2001) p. 1019].

On the whole, the formation of the nanocrystalline structure in commercially pure titanium, described above, in the proposed combination of features of the invention results in the simultaneous increase of strength and ductility and, correspondingly, in the enhancement of its resistance to fatigue failure, and also in the increase of its biocompatibility.

BRIEF DESCRIPTION OF THE DRAWINGS

These and other objects of the invention will be more clearly understood from the ensuing description in conjunction with appended drawings, in which.

DETAILED DESCRIPTION OF THE INVENTION

Figure 1:
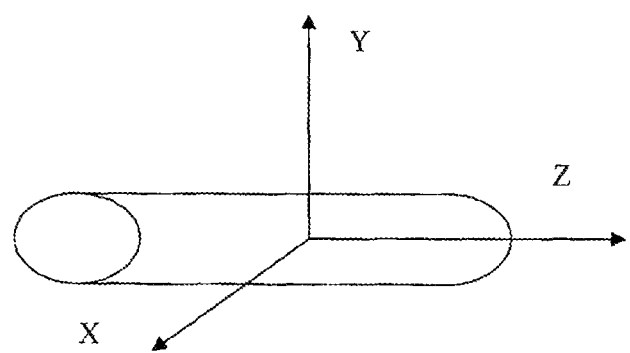
FIG. 1 illustrates a cut-off scheme of the rod made in accordance with the present invention.

A rod of commercially pure titanium is used as a billet. At the first stage of processing the billet is processed via equal-channel angular pressing (ECAP) at a temperature not over 450° C. in 4 passes to achieve the true accumulated strain e≥4 in a die set with the angle of channel intersection ψ=90°. After each pass, the billet is turned around its longitudinal axis clockwise by the angle of 90° in order to provide homogeneity in developing the structure. At this stage, the main refinement of the microstructure takes place in the bulk of the billet without changing its dimensions. At the initial stages of plastic deformation (e=1 after the first ECAP pass), the initial grains are fragmented as a result of generating deformation twins and cells with mostly low-angle dislocation boundaries. With the increase of the true accumulated strain to e=4 (after the 4$^{th}$ ECAP pass), new twins are generated in the structure, and in the course of that further grain fragmentation takes place. At the same time, dislocation walls of cells become more narrow and ordered, their disorientation angle increases, thus contributing to transformation of the cell structure into a grain one. As a result of the structure evolution in the course of ECAP, a grain/subgrain structure forms in titanium. The structure is characterized by strongly non-equilibrium boundaries and high density of grain boundary and lattice dislocations and with the grain size in the range of 0.5 ... 0.7 µm.

After the ECAP, the billets are subjected to thermo mechanical treatment, in the course of which plastic deformation is effected with a gradual temperature decrease in the range of T=450 ... 350° C. with the total accumulated strain from 40 to 80%, the strain rate varying in the range of $10^{-2} ... 10^{-4}$ s$^{-1}$, i.e. under the temperature-rate conditions close to those of superplasticity of the material. Plastic deformation under the described temperature-rate conditions can be realized by such techniques as warm rolling, uniaxial extrusion, die forging. The combination of plastic deformation and heating contributes to a further evolution of the structure obtained as a result of the ECAP: transforming subgrain boundaries into grain boundaries, and thus, increasing the share of high-angle boundaries; generating new grains, decreasing the lattice dislocation densities due to the simultaneous processes of recovery and dynamic recrystallization.

Thus, as a result of the combined treatment, a nanocrystalline structure forms in commercially pure titanium, the share of grains with an average size of 100 ... 500 nm and grain shape coefficient of not over 2 in mutually perpendicular planes making up to 90%, about 60% of them having high-angle boundaries.

Example of Actual Implementation of the Invention.

A rod of commercially pure titanium of the brand CP Grade 4 with a diameter of 40 mm and a length of 150 mm was used as an initial billet. This billet was subjected to ECAP at a temperature of 400° C., in 4 passes in a die set with the angle of channel intersection ψ=90°. The billet after each pass was turned clockwise around its longitudinal axis by the angle of 90°. Then the billet was taken out of the die set and cooled to room temperature, after which it was processed by lathe machining in order to remove a defective layer.

Following the ECAP, the billet was subjected to thermo mechanical treatment, in the course of which plastic deformation by warm rolling was effected with a gradual temperature decrease in the range of T=450 . . . 350° C. with the total accumulated strain of 80%, the strain rate making about $10^{-3}$ $s^{-1}$. As a result of this treatment a rod with a diameter of ~7 mm and a length of ~3000 mm was fabricated.

A microstructure of the samples cut out of this rod was studied with the help of the JEM-100B microscope using the transmission electron microscopy technique. The samples were cut out with the help of electroerosion technique in the shape of plates in the cross and longitudinal sections of the rod. In order to make thin foils the plates were subjected to mechanical thinning to the thickness of 100 μm and a subsequent electrolytic polishing on the Tenupol-5 (Struers) machine at room temperature in the electrolytic solution consisting of perchloric acid ($HClO_4$), butanol ($C_4H_9OH$) and methanol ($CH_3OH$).

Figure 2:
FIG. 2 is a photo of a microstructure of the rod taken in a cross-section.
Figure 3:
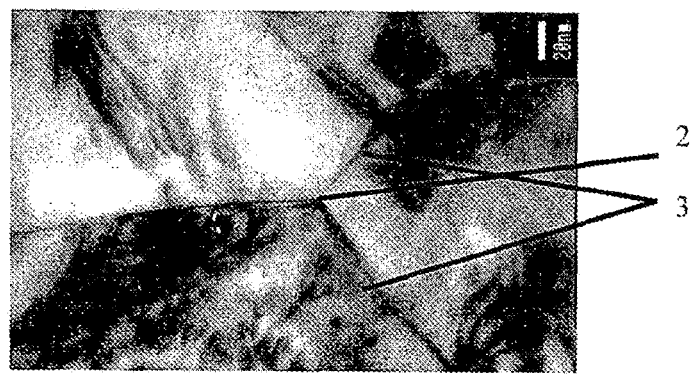
FIG. 3 is a photo of a microstructure of the rod taken in a cross-section and illustrating a grain junction.
Figure 4:
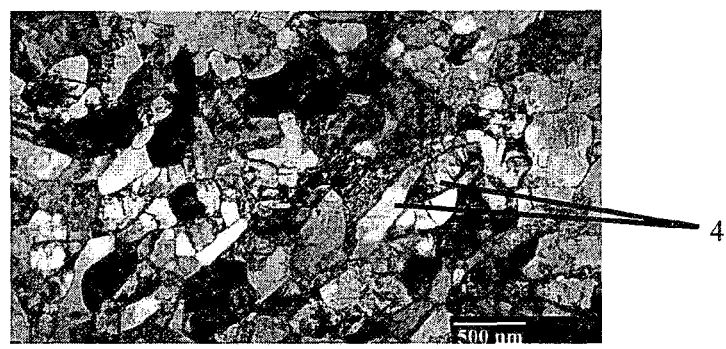
FIG. 4 is a photo of a microstructure of the rod taken in a longitudinal section.

FIG. 1 demonstrates a cut-off scheme of the rod where plane XY—a cross section of the billet and plane ZX—a longitudinal section. The microstructure of the rod is represented by photos in FIGS. 2 and 3 in the cross section, and in FIG. 4 in the longitudinal section. In FIG. 2, it is observed that the grain size (1) in the cross section of the rod makes 150 nm on the average. FIG. 3 shows a triple junction (2) of the grains with high-angle boundaries (3). FIG. 4 demonstrates that in the longitudinal section of the rod, distinct grains (4) are uncovered with an elongated shape, their width-to-length ratio being, however, no more than 2:1.

The table represents results of room-temperature tensile tests conducted on the samples cut from a commercially pure titanium Grade 4 rod made by means of the method according to the present invention. Presented for the sake of comparison are the results of mechanical tests of samples of commercially pure titanium fabricated in accordance with the prior art [G. Kh. Sadikova, V. V. Latysh, I. P. Semenova, R. Z. Valiev Ibid.].

that colonization of fibroblast cells on the surface of titanium increases considerably after nanostructuring. The percentage of the conventional titanium surface occupied by the cells made 53% after 72 hours in comparison to 87% for nanostructural titanium [www.timplant.cz]. These investigations point at a higher osteointegration rate on the nanostructural titanium in comparison to the material in the conventional coarse-grained state.

Thus, the present invention allows forming a nanocrystalline structure in commercially pure titanium, ensuring an enhanced strength, fatigue endurance and biocompatibility of the material and fabricating a rod-shaped billet of this material.

The invention claimed is:

1. Nanostructured commercially pure titanium for biomedicine presenting a nanocrystalline alpha-phase grain structure with a hexagonal close-packed lattice wherein no less than 90% of the grains by volume belong to the grains with a size of 0.1 . . . 0.5 μm and with a grain shape coefficient no more than 2 in mutually perpendicular planes and wherein over 60% of the grains belong to the grains having high-angle boundaries disoriented in relation to the adjacent grains by the angles from 15 to 90°.

2. A method for fabricating a rod of commercially pure titanium with the nanocrystalline structure for biomedicine as claimed in claim 1, the method comprising the steps of:
   providing a billet,
   subjecting the billet to plastic deformation by means of equal channel angular pressing at a temperature of no more than 450° C. with the total accumulated true strain e≥4, and
   subjecting the billet to subsequent additional plastic deformation with the strain degree from 40 to 80%, the additional plastic deformation being carried out with a gradual decrease of temperature in the range of T=450 . . . 350° C. and the strain rate $10^{-2}$ . . . $10^{-4}$ $s^{-1}$.

TABLE

Mechanical properties of commercially pure titanium.

| No | Semi-product state | Ultimate tensile strength, MPa | Yield stress, MPa | Elongation, % | Reduction in area, % | $\sigma_{-1}$ (endurance limit), MPa $N = 10^7$ cycles |
|---|---|---|---|---|---|---|
| 1 | Ti rod with the ultrafine-grained structure in accordance with the prior art | 1150 | 1100 | 11 | 56 | 500 |
| 2 | Ti Grade 4 rod Ø 7 mm with the nanostructure in accordance with the present invention | 1330 ± 10 | 1280 ± 20 | 12 ± 2 | 50 ± 2 | 640 |

It is seen from the table that the mechanical properties of nanostructural titanium made with the use of the present invention are considerably higher than those of ultrafine-grained titanium fabricated in accordance with the prior art.

There have also been conducted experiments on planting human osteoblastic cells CRL—11372 on the surface of conventional coarse-grained and nanostructural samples of commercially pure titanium and the Ti-6Al-4V alloy. It has been demonstrated that adhesion of osteoblastic cells for the nanostructural state is considerably higher when compared to the coarse-grained state of both materials (76% and 15% correspondingly). The investigations of cell behavior demonstrate 3. The method according to claim 2, wherein the step of equal channel angular pressing is carried out in four passes, the billet being turned after each pass around its longitudinal axis by the angle of 90°.

4. The method according to claim 2, wherein the additional plastic deformation is performed by means of warm rolling.

5. The method according to claim 2, wherein the additional plastic deformation is performed by means of uniaxial extrusion.

6. The method according to claim 2, wherein the additional plastic deformation is performed by means of die forging.

7. A method for fabricating a rod of commercially pure nanostructured titanium for biomedicine comprising the steps of:
providing a billet,
subjecting the billet to plastic deformation by means of equal channel angular pressing at a temperature of no more than 450° C. with the total accumulated true strain e≥4, and
subjecting the billet to subsequent thermo-mechanical treatment with the strain degree from 40 to 80% by means of warm rolling at gradually decreasing temperature in the range of T=450 . . . 350° C. and the strain rate $10^{-2}$ . . . $10^{-4}$ $s^{-1}$, to thereby form a nanocrystalline alpha-phase grain structure in the rod with a hexagonal close-packed lattice wherein no less than 90% of the grains by volume belong to the grains with a size of 0.1 . . . 0.5 μm and with a grain shape coefficient no more than 2 in the mutually perpendicular planes, and wherein over 60% of the grains belong to the grains having high-angle boundaries disoriented in relation to the adjacent grains by the angles from 15 to 90°.

8. The method according to claim 7, wherein the step of equal channel angular pressing is carried out in four passes, the billet being turned after each pass around its longitudinal axis by the angle of 90°.

9. The method according to claim 7, further comprising cooling the billet to room temperature and then processing the same by lathe machining to remove a defective layer.

10. A method for fabricating a rod of commercially pure nanostructured titanium for biomedicine comprising:
providing a billet,
subjecting the billet to plastic deformation by means of equal channel angular pressing at a temperature of no more than 450° C. with the total accumulated true strain e≥4,
said plastic deforming by means of equal channel angular pressing being carried out in four passes, the billet being turned after each pass around its longitudinal axis by the angle of 90°, and
subjecting the billet to subsequent thermo-mechanical treatment with the strain degree from 40 to 80% by means of warm rolling at gradually decreasing temperature in the range of T=450 . . . 350° C. and the strain rate $10^{-2}$ . . . $10^{-4}$ $s^{-1}$,
whereby a nanocrystalline alpha-phase grain structure in the rod with a hexagonal close-packed lattice is formed wherein no less than 90% of the grains by volume belong to the grains with a size of 0.1 . . . 0.5 μm and with a grain shape coefficient no more than 2 in the mutually perpendicular planes, and wherein over 60% of the grains belong to the grains having high-angle boundaries disoriented in relation to the adjacent grains by the angles from 15 to 90°.

\* \* \* \* \*